United States Patent [19]

Nebzydoski et al.

[11] 4,283,296

[45] Aug. 11, 1981

[54] AMINE SALT OF N-TRIAZOLYL-HYDROCARBYL SUCCINAMIC ACID AND LUBRICATING OIL COMPOSITION CONTAINING SAME

[75] Inventors: John W. Nebzydoski, Pittsburgh, Pa.; Edwin L. Patmore, Fishkill, N.Y.

[73] Assignee: Texaco Inc., White Plains, N.Y.

[21] Appl. No.: 104,487

[22] Filed: Dec. 17, 1979

Related U.S. Application Data

[63] Continuation-in-part of Ser. No. 935,237, Aug. 21, 1978, abandoned, which is a continuation of Ser. No. 776,689, Mar. 11, 1977, abandoned, which is a continuation of Ser. No. 317,446, Dec. 22, 1972, abandoned.

[51] Int. Cl.$^3$ .................................... C10M 1/46
[52] U.S. Cl. ................... 252/49.9; 252/34; 252/34.7; 252/50; 252/51.5 R; 252/51.5 A; 252/56 S; 548/262; 548/269
[58] Field of Search .............. 252/49.9, 50, 51.5 R, 252/51.5 A, 56 S, 34.7, 34; 548/262, 269

[56] References Cited

U.S. PATENT DOCUMENTS

| | | | |
|---|---|---|---|
| 2,830,021 | 4/1958 | Smith et al. | 252/34 |
| 3,135,765 | 6/1964 | Andress, Jr. et al. | 252/34 X |
| 3,144,460 | 8/1964 | Hosler et al. | 260/308 R |
| 3,235,495 | 2/1966 | Buehler | 252/34.7 X |
| 3,247,111 | 4/1966 | Oberright et al. | 252/34.7 |
| 3,248,398 | 4/1966 | Mühlbauer et al. | 260/308 R |
| 3,256,248 | 6/1966 | Lee | 260/308 R X |
| 3,427,245 | 2/1969 | Hotten | 252/34.7 |
| 3,652,411 | 3/1972 | Commichau | 252/34.7 |
| 3,711,496 | 1/1973 | Matter et al. | 260/308 R |
| 3,790,478 | 2/1974 | Rudston et al. | 252/34 |
| 3,790,478 | 2/1974 | Rudston et al. | 252/34 |
| 3,794,661 | 2/1974 | Boehner et al. | 260/308 R |
| 3,813,400 | 5/1974 | Boyle et al. | 260/308 R X |
| 3,843,531 | 10/1974 | Nebzydoski et al. | 252/34 X |
| 3,897,351 | 7/1975 | Davis et al. | 252/34 |
| 4,064,059 | 12/1977 | Nebzydoski et al. | 252/49.9 |

FOREIGN PATENT DOCUMENTS

| | | | |
|---|---|---|---|
| 530172 | 9/1956 | Canada | 252/34 |
| 1502381 | 11/1966 | France | 252/51.5 A |

Primary Examiner—Andrew Metz
Attorney, Agent, or Firm—Carl G. Ries; Robert A. Kulason; James J. O'Loughlin

[57] ABSTRACT

An amine salt of N-triazolyl-hydrocarbyl succinamic acid represented by the formula:

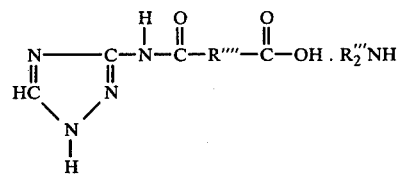

in which R'''' is an alkylene radical having from 2 to 24 carbon atoms and R''' is hydrogen or a hydrocarbyl radical having from 1 to 24 carbon atoms at least one R''' being a hydrocarbyl radical and a lubricating oil composition containing same is provided.

20 Claims, No Drawings

AMINE SALT OF N-TRIAZOLYL-HYDROCARBYL SUCCINAMIC ACID AND LUBRICATING OIL COMPOSITION CONTAINING SAME

This application is a continuation-in-part of application Ser. No. 935,237, filed Aug. 21, 1978, now abandoned which is a continuation of application Ser. No. 776,689 filed Mar. 11, 1977, now abandoned, which is a continuation of application Ser. No. 317,446, filed Dec. 22, 1972, now abandoned.

BACKGROUND OF THE INVENTION

1. Field of Invention

The present invention relates to amine salts of N-triazolyl-hydrocarbyl succinamic acids and to lubricating oil compositions containing same.

The operational efficiency and reliability of an internal combustion engine is vitally dependent on the lubricating oil composition employed in the engine. The oil composition must provide effective lubrication over a wide temperature range including cold and occasionally sub-zero engine starting temperatures, low temperature stop-and-go driving conditions, and high speed, high engine operating temperatures. An effective lubricant must also exhibit thermal stability, anti-wear, load-carrying and anti-oxidation properties for extended operating periods. In the case of gas turbine engines, the lubricating oil composition is subjected to internal engine operating temperatures ranging as high as 500° F. or higher which puts an extreme stress on the stability of the oil.

Because of the noted requirements, lubricating oil compositions are constantly under investigation to improve their effectiveness for providing the required properties as well as to extend the length of their service life. Additive candidates are continuously being introduced into base oils to form new experimental lubricant compositions and the more promising new lubricants identified in screening tests are further tested to determine their effectiveness under representative operating conditions.

2. Description of the Prior Art

It is known in the art that the addition of an azole compound to a synthetic lubricating oil composition will improve the copper corrosion properties of the lubricating composition. The azole type additives, including such compounds as 3-amino-triazole and 4-amino-triazole, are known as copper passivators. It has been theorized that these compounds attach themselves to the surface of the copper substrate to deactivate or reduce the corrosiveness of the copper metal that is in contact with the hot lubricating oil composition. Examples of this are U.S. Pat. No. 4,064,059, U.S. Pat. No. 3,756,952, U.S. Pat. No. 3,247,111 and British Pat. No. 1,180,387 which are incorporated herein by reference.

Despite the extensive art relating to lubricating oil compositions, there still remain problems which are not solved by the compositions known in the art. There is still a need for additives which lead to the production of lubricating oil compositions with improved oxidation resistance, rust inhibiting and metal deactivating properties. None of the prior art lubricating oil compositions which employ azole type additives are completely satisfactory for these purposes.

Accordingly, it is an object of this invention to provide an amine salt of an N-triazolyl hydrocarbyl-substituted succinamic acid which can be incorporated into a lubricating oil composition.

It is also an object of this invention to provide a lubricating oil composition containing the amine salt of an N-triazolyl hydrocarbyl-substituted succinamic acid which exhibits outstanding rust inhibiting properties in addition to thermal and oxidation stability and copper metal passivity.

The advantages and objects of this invention will become apparent to those skilled in the art from the following discussion and accompanying examples.

SUMMARY OF THE INVENTION

It has been found that novel amine salts of N-triazolyl hydrocarbyl-substituted succinamic acids can be prepared by reacting a hydrocarbyl-substituted succinic anhydride with 3-amino-1,2,4-triazole to form an intermediate hydrocarbyl-succinamic acid followed by a reaction of this hydrocarbyl-succinamic acid with a hydrocarbyl amine to form the noted compound. These compounds have excellent stability and are particularly useful as additives in lubricating oil compositions.

Novel lubricating oil compositions which exhibit outstanding rust inhibiting properties together with oxidation stability and corrosion inhibition containing the noted amine salt of an N-triazolyl hydrocarbyl-substituted-succinamic acid are also contemplated.

DESCRIPTION OF THE PREFERRED EMBODIMENTS

In accordance with this invention, an amine salt of an N-triazolyl hydrocarbyl-substituted succinamic acid is prepared in a two-step process. In the first step of the reaction, 3-amino-1,2,4-triazole is reacted with a hydrocarbyl-substituted succinic anhydride to produce as an intermediate reaction product a hydrocarbyl-substituted-N-(3-[1,2,4-triazolyl]) succinamic acid.

The hydrocarbyl-substituted succinic anhydride reactant is represented by the following formula:

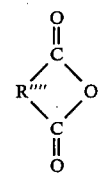

in which R'''' represents a hydrocarbyl radical having from 2 to 24 carbon atoms. The hydrocarbyl radical in the succinic anhydride can be saturated or unsaturated. A preferred hydrocarbyl-substituted succinic anhydride is one in which the hydrocarbyl radical represented by R'''' has from 2 to 18 carbon atoms.

A more preferred hydrocarbyl-substituted succinic anhydride is represented by the formula:

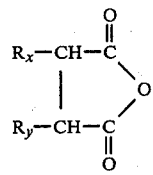

in which $R_x$ and $R_y$ alternately represent hydrogen and a monovalent unsaturated hydrocarbon radical having from 6 to 16 carbon atoms.

Examples of suitable hydrocarbyl-substituted succinic anhydride reactants include dipropenyl succinic anhydride, tripropenyl succinic anhydride, tetrapropenyl succinic anhydride, pentapropenyl succinic anhydride, hexapropenyl succinic anhydride, decenyl succinic anhydride, t-octyl succinic anhydride, dodecenyl succinic anhydride, tetradecyl succinic anhydride, tetradecenyl succinic anhydride, hexadecenyl succinic anhydride and octadecenyl succinic anhydride.

The reaction between 3-amino-1,2,4-triazole and the prescribed hydrocarbon substituted succinic anhydride to produce an N-triazolyl-hydrocarbyl-substituted succinamic acid is depicted in the following formulas:

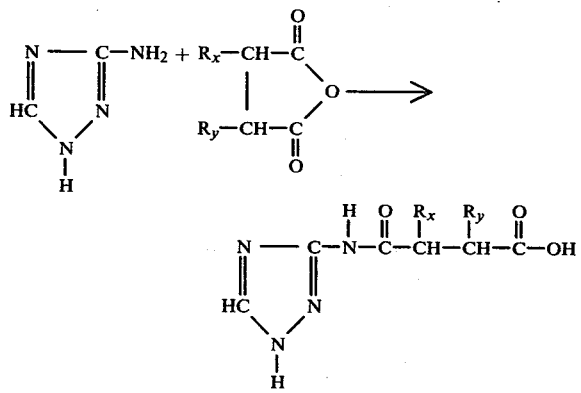

in which $R_x$ and $R_y$ have the values noted above.

The above reaction is preferably conducted using approximately equimolar amounts of the 3-amino-1,2,4-triazole optionally written as 3-amino-1H,-1,2,4-triazole and the hydrocarbyl- or alkenyl-substituted succinic anhydride reactants. The molar ratio may be varied by employing from about 0.7 to 1.3 moles of the 3-amino-1,2,4-triazole per mole of the hydrocarbyl-substituted succinic anhydride.

This reaction is preferably conducted in the presence of an inert solvent. Any inert hydrocarbon solvent that is liquid under the reaction conditions is generally satisfactory. Examples of solvents which can be used to conduct this reaction include benzene, toluene, n-heptane, xylene and similar aliphatic and aromatic solvents.

This reaction can be conducted at a temperature ranging from room temperature up to the decomposition temperature of the reactants. It is preferred, however, to conduct this reaction at the reflux temperature of the solvent being employed for a sufficient length of time to complete the reaction.

The following examples illustrate the preparation of the intermediate or precursor N-(3-[1,2,4-triazole]) hydrocarbyl-substituted succinamic acid.

EXAMPLE 1

Mixture of 2-and 3-Dodecyl-N-(3-[1,2,4-Triazolyl]) Succinamic Acid 26.8 g. (0.1 mole) dodecyl succinic anhydride, 8.4 g. (0.1 mole) 3-amino-1H-1,2,4-triazole and 150 ml. of benzene were heated at reflux for four hours with stirring. Concentration under reduced pressure afforded the product. Yield: 35 g. % N Calc. 15.9 Found: 16.6.

EXAMPLE 2

Mixture of 2-and 3-Tetrapropenyl-N-(3-[1,2,4-Triazolyl]) Succinamic Acid 8.4 g. (0.1 mole) of 3-amino-1H-1,2,4-triazole, 26.6 g. (0.1 mole) tetrapropenyl succinic anhydride and 100 ml. of benzene were heated at reflux for four hours with stirring. Concentration under reduced pressure afforded the product. Yield=34 g. % N Calc. 15.9 Found 16.0.

EXAMPLE 3

Mixture of 2-and 3-Tetradecenyl-N-(3-[1,2,4-Triazolyl]) Succinamic Acid 14.5 g. of tetradecenyl succinic anhydride, 4.2 g. of 3-amino-1H-1,2,4-triazole and 75 ml. of benzene were heated at reflux for two hours. Filter off small amount of benzene insolubles. Concentrate filtrate to afford the product as a waxy solid. %N Calc.—14.8 Found—14.1.

Other typical intermediate or precursor N-(3-[1,2,4-triazolyl]) hydrocarbyl-substituted succinamic acids include 2-decenyl-N-(3-[1,2,4-triazolyl]) succinamic acid, 2- and 3-octenyl-N-(3-[1,2,4-triazolyl]) succinamic acid, 2- and 3-hexadecenyl-N-(3-[1,2,4-triazolyl]) succinamic acid, 3-octadecenyl-N-(3-[1,2,4-triazolyl]) succinamic acid, 2-and 3-eicosenyl-N-(3-[1,2,4-triazolyl]) succinamic acid and 2- and 3-dodecenyl-N-(3-[1,2,4-triazolyl]) succinamic acid.

The intermediate N-triazolyl hydrocarbyl-substituted succinamic acid does not possess the required properties for the contemplated lubricating oil composition of this invention and must be reacted with a hydrocarbyl amine defined below to produce the prescribed amine salt of N-triazolyl hydrocarbyl succinamic acid.

The amine salts of N-triazolyl-hydrocarbyl succinamic acids impart valuable rust inhibiting properties to lubricating oil compositions while the N-triazolyl hydrocarbyl succinamic acids do not. This difference in performance is not fully understood but may be accounted for by the different chemical and structural features of the amine salts.

The hydrocarbyl amine reactant which can be employed in the second step of the process for the preparation of the prescribed novel amine salt compound of the invention is a primary or secondary aliphatic or aromatic amine represented by the formula:

in which $R'''$ is a hydrogen or a hydrocarbyl radical having from 1 to 24 carbon atoms, at least one $R'''$ being a hydrocarbyl radical.

The preferred amine is a saturated aliphatic hydrocarbon primary amine represented by the formula $R'''NH_2$ in which $R'''$ represents a monovalent saturated aliphatic hydrocarbon radical having from 1 to 22 carbon atoms. The most preferred amines are those in which $R'''$ is a monovalent aliphatic hydrocarbon radical having from 8 to 18 carbon atoms.

Examples of suitable amines for preparing the amine salt of N-triazolyl hydrocarbyl succinamic acid include methylamine, ethylamine, propylamine, n-butylamine, n-hexylamine, n-octylamine, t-octylamine, decylamine, dodecylamine, tetradecylamine, $C_{11}$–$C_{14}$-tertiary alkyl primary amine, $C_{18}$–$C_{22}$-tertiary alkyl primary amine, stearylamine, oleylamine, laurylamine, dicyclohexylamine, dioctylamine and didodecylamine.

The prescribed hydrocarbyl amine and N-triazolyl hydrocarbyl succinamic acid are mixed neat or in an inert hydrocarbon solvent for sufficient time to complete the formation of the prescribed amine salt of N-triazolyl hydrocarbyl succinamic acid. Equimolar amounts of the hydrocarbyl amine and of the N-triazolyl hydrocarbyl succinamic acid are preferably employed in this reaction. It is possible, however, to employ from about 0.75 to 1.25 moles of hydrocarbylamine with a mole of N-triazolyl hydrocarbyl succinamic acid to produce a product containing a major amount of the prescribed amine salt of N-triazolyl hydrocarbyl succinamic acid. This reaction is facilitated by using one of the inert solvents employed in the first step of the reaction using an elevated temperature ranging from room temperature to the reflux temperature of the solvent.

The following examples illustrate amine salts of N-triazolyl hydrocarbyl succinamic acids which can be prepared by reacting an intermediate hydrocarbyl-N-(3-[1,2,4-triazolyl]) succinamic acid with a hydrocarbyl amine by refluxing approximately equimolar amounts of said amine and said intermediate in benzene for a reaction period of 1½ to 2½ hours. A quantitative yield of the product is obtained on removal of the solvent under reduced pressure.

EXAMPLE 4

Approximately equimolar amounts of N-(3-[1,2,4-triazolyl])-2-dodecen-1-yl succinamic acid and tertiary octyl amine were reacted as described above to form the tert-octylamine salt of N-(3-[1,2,4-triazolyl])-2-dodecen-1-yl succinamic acid represented by the formula:

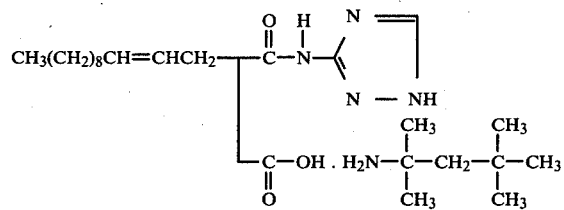

This compound was amber colored when molten and white in powder form. It had a melting point of 77°–82° C.

| Elemental Analysis: | Found | Theory |
|---|---|---|
| % N | 14.4 | 14.6 |
| % C | 65.1 | 65.1 |
| % H | 10.2 | 10.2 |

The infrared spectrum was consistent with the compound structure and gave the following band values:

| IR band, cm$^{-1}$ | Assignment |
|---|---|
| 1540 | Amide II |
| 1580 | $-CO_2^{\ominus}$ |
| 1630 | $-N=N-$ |
| 1680 | Amide I |
| 2720 | $NH_2^+$ |

EXAMPLE 5

Tertiary Octyl Amine Salt of 2-Dodecyl-N-(3-[1,2,4-Triazolyl])-Succinamic Acid and the corresponding 3-Dodecyl derivative.

EXAMPLE 6

Tertiary Octyl Amine Salt of 2-Tetrapropenyl-N-(3-[1,2,4-Triazolyl])-Succinamic Acid and the corresponding 3-Tetrapropenyl derivative.

EXAMPLE 7

Tertiary $C_{18-22}$ Alkyl Amine Salt of 2-Dodecyl-N-(3-[1,2,4-Triazolyl])-Succinamic Acid and the corresponding 3-Dodecyl derivative.

EXAMPLE 8

Tertiary $C_{11-14}$ Alkyl Amine Salt of 2-Dodecyl-N-(3-[1,2,4-Triazolyl])-Succinamic Acid and the corresponding 3-Dodecyl derivative.

EXAMPLE 9

Dicyclohexyl Amine Salt of 2-Dodecyl-N-(3-[1,2,4-Triazolyl])-Succinamic Acid and the corresponding 3-Dodecyl derivative.

EXAMPLE 10

Secondary $C_{15}$ alkyl amine salt of 2-dodecyl-N-(3-[1,2,4-triazolyl]) succinamic acid.

EXAMPLE 11 n-Butyl amine salt of N-(3-[1,2,4-triazolyl])-2-dodecen-1-yl succinamic acid.

EXAMPLE 12 n-Hexylamine salt of N-(3-[1,2,4-triazolyl])-2-dodecen-1-yl succinamic acid.

EXAMPLE 13 n-Octylamine salt of N-(3-[1,2,4-triazolyl])-2-dodecen-1-yl succinamic acid.

EXAMPLE 14 n-Decylamine salt of N-(3-[1,2,4-triazolyl])-2-dodecen-1-yl succinamic acid.

The novel amine salt of N-triazolyl-hydrocarbyl succinamic acid of the invention is highly effective as an anti-rust additive as well as providing other valuable properties in a lubricating oil composition. The oil substrate may be a mineral, a synthetic or mixed mineral-synthetic lubricating oil. The synthetic oil substrates include ester base oils, alkylene polymers, alkylene epoxide type polymers, alkylbenzenes, polyphenyls and the like.

The hydrocarbon mineral oil base can be a paraffin base, a naphthene base or a mixed paraffin-naphthene base oil. The mineral lubricating oil base will generally have been subjected to solvent refining to improve its lubricity and viscosity temperature relationship as well as solvent dewaxing to remove waxy components and improve the pour of the oil. Generally, mineral lubricating oils having an SUS viscosity at 100° F. between 50 and 500 may be used in the formulation of the improved lubricants of this invention, although the preferred viscosity range will be from about 70 and 300 SUS at 100° F. A blend of mineral base oils can be employed to provide a suitable base oil for either a single or multigrade motor oil. The base oil will constitute from about 85 to 99% or more of the lubricant composition.

The lubricating composition of the invention can contain from about 0.01 to 5 percent by weight of the prescribed amine salt additive. It is preferred, however, to employ from about 0.05 to 0.5 weight percent. This lubricant composition may also contain anti-wear, load carrying, anti-oxidation, viscosity index improving and detergentdispersant additives each in the amounts within the range from about 0.1 to 10% by weight.

The following examples are illustrative of the lubricating compositions of the invention, all percentages being by weight.

EXAMPLE 15

A mineral lubricating oil having an SUS of 100 at 100° F. containing 0.05% of the product of Example 4.

EXAMPLE 16

A paraffin base mineral lubricating oil having an SUS of 125 at 100° F. containing 0.1 weight percent of the tertiary octylamine salt of 2-dodecyl-N-(3-[1,2,4-triazolyl]) succinamic acid.

EXAMPLE 17

A mixed paraffinic-naphthenic mineral lubricating oil having an SUS viscosity of 100 at 100° F. containing 0.2% of the tertiary octylamine salt of 2-tetrapropenyl-N-(3-[1,2,4-triazolyl]) succinamic acid.

EXAMPLE 18

A synthetic lubricating oil consisting of an ester base formed from pentaerythritol and a mixture of C5 to C9 monocarboxylic acids having a viscosity of 25.6 cs at 100° F. containing 0.05 weight percent of the product of Example 4.

EXAMPLE 19

A mixed paraffinic mineral oil and synthetic pentaerythritol ester base lubricating oil having a viscosity of 100 at 100° F. containing 0.5 weight percent of the tertiary octylamine salt of 2-dodecenyl-N-(3-[1,2,4-triazolyl]) succinamic acid.

The particularly preferred lubricating oil composition of the invention is a synthetic aliphatic ester base lubricating oil composition. In general, the base oil employed in this type of lubricant comprises an ester base fluid prepared from pentaerythritol or trimethylolpropane and a mixture of aliphatic hydrocarbon monocarboxylic acids. The preferred hydrocarbon monocarboxylic acids for forming the base oil or ester base fluid are the straight-chain or branched-chain aliphatic monocarboxylic acids having from about 2 to 18 carbon atoms and preferably having from about 5 to 10 carbon atoms. Examples of suitable specific aliphatic acids include acetic acid, propionic acid, butyric acid, valeric acid, isovaleric acid, caproic acid, decanoic acid and the like. Generally, an ester based lubricating oil composition will contain a base oil or ester base fluid formed from a mixture of esters such as the esters formed from pentaerythritol and a mixture of C5 to C10 aliphatic monocarboxylic acids selected to provide desired viscosity properties. An example of a specific ester base fluid is a tetraester formed from pentaerythritol and a mixture of aliphatic monocarboxylic acids comprising 38% valeric acid, 13% 2-methylpentanoic acid, 32% octanoic acid and 17% pelagonic acid. Another effective ester base fluid is the triester formed from trimethylolpropane and a mixture of aliphatic monocarboxylic acids consisting of 2% valeric, 9% caproic, 13% heptanoic, 7% octanoic acid, 3% caprylic acid, 65% pelagonic acid and 1% capric acid.

An ester base blend is employed for preparing synthetic aircraft turbine lubricating oil compositions. A conventional ester base blend comprises the base oil or ester base fluid and from about 0.3 to 5% by weight of a naphthylamine derivative, such as phenyl alpha naphthylamine or an alkyl or alkaryl-substituted phenyl naphthylamine in which the alkyl and alkaryl radicals have from 1 to 12 carbon atoms, from about 0.3 to 5% of a dialkyldiphenylamine in which the alkyl radicals have from 1 to 12 carbon atoms and particularly from 4 to 12 carbon atoms, from about 0.25 to 10 weight percent of a trihydrocarbyl phosphate in which the hydrocarbyl radical contains a aryl ring and contains from about 6 to 18 carbon atoms, and, optionally, from about 0.04 to 2 weight percent of a polyhydroxy-substituted anthraquinone, such as quinizarin. A very small proportion, e.g., from about 1 to 50 ppm (parts per million) of a silicone anti-foam agent, such as dimethyl silicone and diethyl silicone can also optionally be employed.

Concentrates of the novel additive of the invention can be prepared using a mineral oil, synthetic oil, or mixed oil base containing from 5 to 50 weight percent of the additive.

The following examples illustrate specific ester base blends which are useful for preparing synthetic lubricating oil compositions of the invention.

EXAMPLE 20

Ester Base Blend A

An ester base blend was prepared consisting of 1.0% p,p'-di-tert.-octyldiphenylamine, 1.5 weight percent of N-(p-t-octylphenyl)-1-naphthylamine, 2.0 weight percent of tricresylphosphate and the balance a pentaerythritol ester base oil made from pentaerythritol and a mixture of aliphatic monocarboxylic acids having from 5 to 9 carbon atoms which ester base oil had viscosities in centistokes of 5.01 at 210° F., 25.6 at 100° F. (ASTM Method D 445) and 7005 at $-40°$ F. and a viscosity index of 140.

EXAMPLE 21

Ester Base Blend B

Ester base blend B consisted of 1.0 weight percent of phenyl alpha naphthylamine, 1.0 weight percent of p,p'-di-tert.-octyldiphenylamine, 2.0 weight percent tricresyl phosphate, 0.1 weight percent quinizarin and the balance about 95.8 weight percent of an ester base oil formed from pentaerythritol and a mixture of aliphatic monocarboxylic acid having from 5 to 10 carbon atoms, said ester base oil having kinematic viscosities in centistokes of about 5.10 at 210° F. and about 24.5 at 100° F.

The rust-inhibiting properties of a lubricating oil composition of the invention was determined by preparing a synthetic lubricating oil composition and submitting it for testing against Military Specifications MIL-L-2369.

EXAMPLE 22

A pentaerythritol-aliphatic ester base lubricating oil composition was prepared by blending 0.1 weight percent of the additive of Example 4 into Ester Base Blend B to form a synthetic lubricating oil composition, designated Synthetic Lubricant B. This lubricant was then tested for rustinhibiting properties.

Synthetic Lubricant B passed both the Navy Laboratory Rust Test and MIL-L-23699 Bench Tests. The same lubricant was further tested by an independent Research Institute in the J-57 Turbine Engine Simulator Test which it passed with a cleaner performance than a qualified MIL-L-23699 oil.

Used oil samples of Lubricant B from both the Erdco Bearing Test and from the Navy's T63 Engine Test were further tested in the Navy Laboratory Rust Test and found to have no apparent loss in rust protective properties.

Ester base oil compositions of the invention based on Ester Base Blend A were tested in the 400° F./72 hour and 425° F./48 hour Oxidation-Corrosion Tests in accordance with Method 5308.4 a Federal Test Method and Standard No. 791a (issued December 31, 1961) except for modifications to conform to MIL-L-23699B specifications.

EXAMPLE 23

Lubricating oil compositions were prepared by blending 0.1 weight percent each of tertiary octyl amine salts of 2-dodecyl-N-(3-[1,2,4-triazolyl])-succinamic acid, tertiary octyl amine salt of 2-tetrapropenyl-N(3-[1,2,4-triazolyl])-succinamic acid, tertiary $C_{18-22}$ alkyl amine salt of 2-dodecyl-N-(3-[1,2,4-triazolyl])-succinamic acid, and dicyclohexyl amine salt of 2-dodecyl-N-(3-[1,2,4-triazolyl])-succinamic acid into Ester Base Blend A to form synthetic lubricant compositions. These lubricant compositions were then tested in the 400° F./72 hour and 425° F./48 hour Oxidation-Corrosion Tests. All of these lubricant compositions were found to possess outstanding oxidation and corrosion-inhibiting properties in these industry adopted tests.

The novel amine salts of N-triazolyl-hydrocarbyl succinamic acid of the invention are surprisingly effective as additives for lubricating oil compositions. A particularly unexpected result was the discovery of their rustinhibiting properties which promises to provide new classes of lubricating oil compositions needed to satisfy military aircraft requirements.

We claim:

1. An amine salt of N-triazol hydrocarbyl succinamic acid represented by the formula

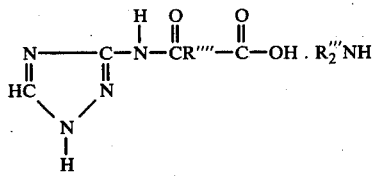

in which $R''''$ is an alkylene radical having 2 carbon atoms and $R'''$ is hydrogen or an aliphatic hydrocarbon radical having from 1 to 24 carbon atoms, at least one $R'''$ being a hydrocarbon radical.

2. A compound according to claim 1 in which at least one $R'''$ is an aliphatic hydrocarbon radical having from 8 to 18 carbon atoms.

3. A compound according to claim 1 in which at least one $R'''$ is a tertiary aliphatic hydrocarbon radical having from 8 to 14 carbon atoms.

4. Tertiary octylamine salt of N-(3-[1,2,4-triazolyl])-$C_{12}$ hydrocarbylsuccinamic acid.

5. Tertiary octylamine salt of N-(3-[1,2,4-triazolyl])-$C_{8-16}$ hydrocarbylsuccinamic acid.

6. Tertiary octylamine salt of N-(3-[1,2,4-triazolyl])-2-dodecen-1-ylsuccinamic acid.

7. Tetradecylamine salt of N-(3-[1,2,4-triazolyl])-2-tetradecen-1-ylsuccinamic acid.

8. Tertiary decylamine salt of N-(3-[1,2,4-triazolyl])-$C_{12}$ hydrocarbylsuccinamic acid.

9. Tertiary dodecylamine salt of N-(3-[1,2,4-triazolyl])-decen-1-ylsuccinamic acid.

10. A lubricating oil composition comprising a major portion of a base oil having lubricating properties and from about 0.01 to 5 weight percent of an amine salt of N-triazolyl hydrocarbyl succinamic acid represented by the formula:

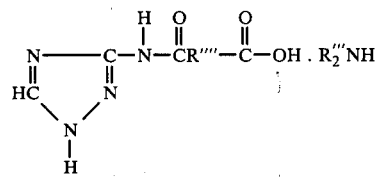

in which $R''''$ is an alkylene radical having 2 carbon atoms and $R'''$ is hydrogen or an aliphatic hydrocarbon radical having from 1 to 24 carbon atoms, at least one $R'''$ being a hydrocarbon radical.

11. A lubricating oil composition according to claim 10 in which at least one aliphatic hydrocarbon radical in said compound has from 8 to 18 carbon atoms.

12. A lubricating oil composition according to claim 10 in which at least one aliphatic hydrocarbon radical compound is a tertiary aliphatic hydrocarbon radical having from 8 to 14 carbon atoms.

13. A lubricating oil composition according to claim 10 in which said amine salt is a tertiary octyl amine salt of N-(3-[1,2,4-triazolyl])-$C_{12}$ alkylsuccinamic acid.

14. A lubricating oil composition according to claim 10 in which said amine salt is a tertiary octylamine salt of N-(3-[1,2,4-triazolyl])-$C_{8-16}$ hydrocarbylsuccinamic acid.

15. A lubricating oil composition according to claim 10 in which said amine salt is a tertiary octylamine salt of N-(3-[1,2,4-triazolyl])-2-dodecen-1-ylsuccinamic acid.

16. A lubricating oil composition according to claim 10 in which said amine salt is a tetradecylamine salt of N-(3-[1,2,4-triazolyl])-3-tetradecen-1-ylsuccinamic acid.

17. A lubricating oil composition according to claim 10 in which said amine salt is a tertiary decylamine salt of N-(3-[1,2,4-triazolyl])-$C_{12}$ hydrocarbyl succinamic acid.

18. A lubricating oil composition according to claim 10 in which said amine salt is a tertiary dodecylamine salt of N-(3-[1,2,4-triazolyl])decen-1-ylsuccinamic acid.

19. An oil concentrate of the amine salt of claim 1 comprising from about 5.0 to 50 weight percent of said amine salt and the balance comprising an oil substrate consisting of a mineral, synthetic or mixed mineral-synthetic oil base.

20. A synthetic lubricating oil composition comprising a major portion of an aliphatic ester base oil having lubricating properties formed from the reaction of pentaerythritol or trimethylolpropane and a saturated hydrocarbyl monocarboxylic acid having from 2 to 18 carbon atoms per molecule, containing A. From about 0.01 to 0.5 weight percent of an amine salt of a substituted 3-aminotriazole represented by the formula:

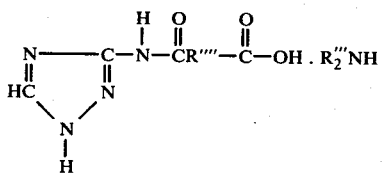

in which R'''' is an alkylene radical having 2 carbon atoms and R''' is hydrogen or an aliphatic hydrocarbon radical having from 1 to 24 carbon atoms, at least one R''' being a hydrocarbon radical.

B. From about 0.3 to 5 percent by weight of the lubricating oil composition of a phenyl naphthylamine or an alkyl or alkaryl-substituted phenyl naphthylamine in which the alkyl and alkaryl radicals have from 1 to 12 carbon atoms.

C. From about 0.3 to 5 percent of a dialkyldiphenylamine in which the alkyl radical has from 4 to 12 carbon atoms, and D. From about 0.25 to 10 percent of a trihydrocarbyl phosphate in which said hydrocarbyl radical contains an aryl ring and contains from about 6 to 18 carbon atoms.

* * * * *